United States Patent
Neagle, III

(10) Patent No.: US 10,984,895 B2
(45) Date of Patent: Apr. 20, 2021

(54) SYSTEM AND METHOD FOR HEALTH AND WELLNESS MOBILE MANAGEMENT

(71) Applicant: Pharmalto, LLC, Plano, TX (US)

(72) Inventor: Charles E. Neagle, III, Plano, TX (US)

(73) Assignee: Pharmalto, LLC, Plano, TX (US)

(*) Notice: Subject to any disclaimer, the term of this patent is extended or adjusted under 35 U.S.C. 154(b) by 865 days.

(21) Appl. No.: 13/916,022

(22) Filed: Jun. 12, 2013

(65) Prior Publication Data

US 2014/0358018 A1    Dec. 4, 2014

Related U.S. Application Data

(63) Continuation-in-part of application No. 13/908,179, filed on Jun. 3, 2013.

(51) Int. Cl.
| | | |
|---|---|---|
| G16H 10/60 | (2018.01) | |
| G16H 40/63 | (2018.01) | |
| G16H 20/30 | (2018.01) | |
| G16H 40/67 | (2018.01) | |
| G16H 20/10 | (2018.01) | |
| G16H 20/60 | (2018.01) | |

(Continued)

(52) U.S. Cl.
CPC .......... *G16H 10/60* (2018.01); *A61B 5/0004* (2013.01); *A61B 5/082* (2013.01); *A61B 5/091* (2013.01); *A61B 5/097* (2013.01); *A61B 5/742* (2013.01); *G16H 20/30* (2018.01); *G16H 40/63* (2018.01); *G16H 40/67* (2018.01); *G16H 20/10* (2018.01); *G16H 20/60* (2018.01)

(58) Field of Classification Search
CPC .. G06Q 50/22–24; A61B 5/097; A61B 5/082; G16H 10/60
See application file for complete search history.

(56) References Cited

U.S. PATENT DOCUMENTS 7,949,545 B1* 5/2011 Madras et al. ............ 705/3
2005/0081601 A1* 4/2005 Lawson .................. 73/23.3
(Continued)

OTHER PUBLICATIONS

Spirometer—The Smartphone Physical, www.smartphonephysical.org/spirometer.html.
(Continued)

*Primary Examiner* — Sheetal R Paulson
(74) *Attorney, Agent, or Firm* — Wei Wei Jeang; Grable Martin Fulton PLLC

(57) ABSTRACT

A system for health and wellness mobile management comprises a database operable to store a health and wellness data record associated with a patient/data owner, a content management system adapted to strictly control access to the health and wellness data record stored in the database according to access rules set by the patient, a web interface adapted to interface with information requesters submitting requests for access to the health and wellness data record via a web application, an external connect interface adapted to interface with external systems and applications for receiving health and wellness data associated with the patient, a prescription interface adapted to receive a pharmaceutical prescription for the patient submitted by a healthcare provider, and a handheld physiological parameter measurement device adapted to wirelessly communicate with a computing device executing the web application.

26 Claims, 6 Drawing Sheets

(51) Int. Cl.
  *A61B 5/08* (2006.01)
  *A61B 5/091* (2006.01)
  *A61B 5/097* (2006.01)
  *A61B 5/00* (2006.01)

(56) References Cited

U.S. PATENT DOCUMENTS

| | | | |
|---|---|---|---|
| 2005/0182661 A1* | 8/2005 | Allard et al. | 705/3 |
| 2006/0136197 A1* | 6/2006 | Oon | 704/9 |
| 2011/0001605 A1* | 1/2011 | Kiani et al. | 340/5.6 |

OTHER PUBLICATIONS

Wikipedia, the free encyclopedia—Breath carbon monoxide, en.wikipedia.org/wiki/Breath_carbon_monoxide.
Wikipedia, the free encyclopedia—Spirometer, en.wikipedia.org/wiki/Spirometer.
Thor Medical Systems—THOR Laboratories—Thormed R&D—WaveFront Spirometry—WaveFront Flow Meter, www.thormed.com/index.php?page=products&id=spiro4.
microdaq.com, Carbon Monoxide (CO) Data Logger with USB Interface—EasyLog CO Data Recorder, www.microdaq.com/lascar/co_data_logger.php.
kickstarter.com, NODE: a modular, handheld powerhouse of sensors by George Yu—Kickstarter, www.kickstarter.com/projects/108684420/node-a-modular-handheld-powerhouse-of-sensors.
testbreath.com, Smoking Cessation Testing :offering non-invasive solutions for all your gas detection needs, including hydrogen breath monitors, carbon-monoxide testers a . . . , www.testbreath.com/smoking-cessation-testing.asp.

* cited by examiner

SYSTEM AND METHOD FOR HEALTH AND WELLNESS MOBILE MANAGEMENT

RELATED APPLICATIONS

The present disclosure is a continuation-in-part application of U.S. Non-Provisional patent application Ser. No. 13/908,179 entitled System and Method for Health and Wellness Mobile Management, filed on Jun. 3, 2013.

FIELD

The present disclosure relates the field of healthcare management, and more particularly to a system and method for health and wellness mobile management.

BACKGROUND

In the 21st century, the Internet and the World Wide Web have become an increasingly important component of all types of communications. Internet penetration in North America is over 78%, and there are over 2.4 billion Internet users worldwide. In other words, a third of the world's population are Internet users. People are spending more and more time online, surfing the web, watching videos, uploading photographs, looking up information, and socializing on social networking sites. Along with the availability of web-enabled computing devices like the mobile telephone (formerly called smart telephones or personal digital assistants or PDAs), gaming devices, tablet computers, laptop computers, desktop computers, etc., the Internet is more accessible than ever before.

In 2008, people in the United States spent $234 billion on prescription medicine. Over $4.5 billion is spent annually on errors in the administration of medicines, or on unintended interactions and insurance or Medicare/Medicaid fraud and abuse. This nearly $5 billion is dwarfed by the estimate published by the New England Health Care Institute of $290 billion in annual costs associated with non-compliance, under-treatment, and non-treatment of diseases in the United States. With rising costs in healthcare, solutions are sought to control or reduce health-related expenses while improving patient care.

DETAILED DESCRIPTION

Figure 1:
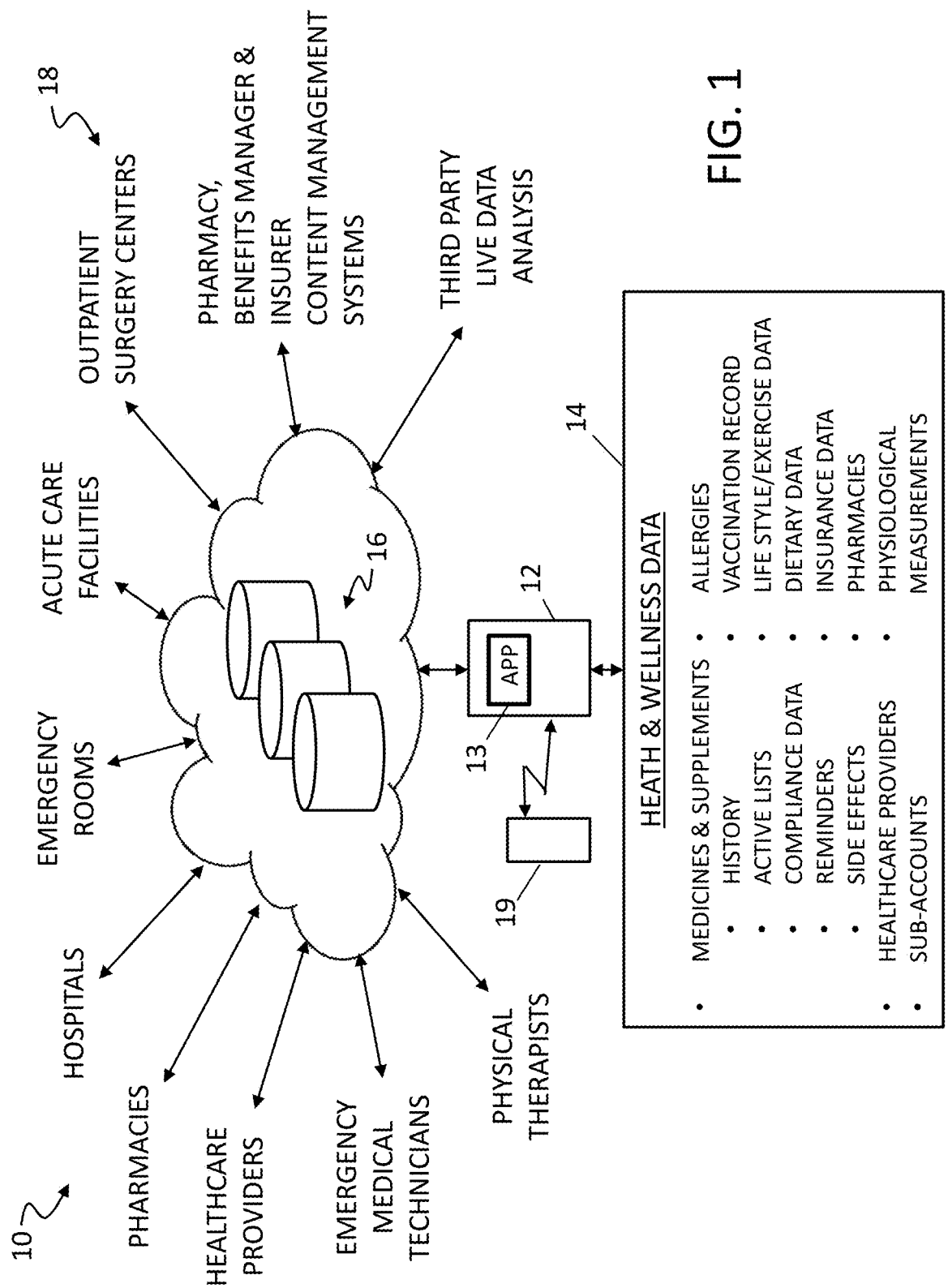
FIG. 1 is a simplified diagram illustrating a health and wellness mobile management system and method according to an exemplary embodiment of the present disclosure.

FIG. 1 is a simplified diagram illustrating a health and wellness mobile management system and method 10 according to an exemplary embodiment of the present disclosure. The system 10 is patient-centric resource that puts the patient's health and wellness data easily within reach of the patient, such as via a software application or app 13 executing on a computing device 12 such as a mobile telephone, mobile gaming device, tablet computer, laptop computer, desktop computer, or other suitable computing devices or platforms in existence now or developed later. The health and wellness data belong to the patient or a legal guardian of the patient, rather than the healthcare providers. The ownership of an account and the data may be transferred to another individual. For example, a dependent account and health and wellness data associated with a minor may be owned by a legal guardian or parent and associated with his/her account, but when the child reaches 18 years old, the account and health and wellness data ownership may be automatically transferred or can be directed to ensure proper ownership of the health and wellness data. Further, the patient has control to give others permission or authorization to access all or a subset of this data.

The patient may easily access a variety of health and wellness data 14, including information relating to medicines and supplements, such as medical history, active lists, compliance data, reminders, ineffective medicine, and side effects. The data also include information about the healthcare providers, pharmacies, sub-accounts, allergies, vaccination record, lifestyle and exercise data, dietary data, laboratory data, imaging data, medical charts, health parameters (blood pressure, glucose, risky addiction or behavior such as smoking cessation monitoring), legal document data (living will, do not resuscitate directives, power of attorney, etc.), and insurance data. These data are stored in one or more databases 16 accessible via the Internet, such as in cloud data stores or cloud databases.

These health and wellness data may originate from a wide variety of sources 18, including, in no particular order, physical therapists, emergency medical technicians, healthcare providers, pharmacies, hospitals, emergency rooms, acute care facilities, laboratories, outpatient surgery centers, pharmacy, benefits manager and insurer content management systems, and third party live data analysis systems. The above are examples provided for illustrative purposes and other types of data related to the patient's health and wellness may be incorporated.

Numerous efforts have been attempted to curtail smoking, ranging from hypnosis, peer support groups, negative reinforcement, biofeedback, nicotine gum and patches, prescription medication, electronic cigarettes, and counseling. While some of these aids have been helpful, recidivism is high and thus early intervention when risky behavior is initially resumed would significantly improve the odds of quitting. Additionally, because many health and life insurance policies set the cost of premiums based on factors including cigarette smoking, the ability to confirm cessation compliance and thus qualify for risk-adjusted health premium is of importance.

The computing device 12 is further operable to communicate, preferably wirelessly, with a variety of external monitoring devices 19. The external monitoring devices 19 may be used for compliance and verification purposes. For example, an external monitoring device 19 may be a device that is operable to measure lung function (e.g., a spirometer) and carbon monoxide (CO) of a patient, which may be used to detect smoking cessation compliance. The combined spirometer and CO sensor, hereinafter referred to as home smoking cessation monitoring device, is operable to measure the volume of air as well as the CO content of inhaled and/or exhaled breath of a patient. Data from the first measurement can be used to determine pulmonary capacity and function (and indirectly oxygen saturation level), and data from the second measurement can be used to determine the amount of blood CO or CO poisoning in the patient. In a patient that has quit smoking, such monitoring should see improved lung capacity and decreasing CO poisoning. Acute changes in the CO level is an especially good assessment of cessation compliance as CO level will immediately rise if the patient smokes and remain elevated for 24-48 hours. Therefore, the home smoking cessation monitoring device can verify that the patient has continued with smoking cessation efforts.

The home smoking cessation monitoring device may include a mouthpiece into which the patient would inhale and exhale. The handheld device includes microprocessor operable to execute software code performing logic and mathematical algorithms to compute quantities that assess the patient's lung function and blood CO content. The device may include a display screen that displays operating instructions, data quantities, and graphical output, for example. The display screen may be touch-sensitive to receive user input. The device may also include a data port such as a USB port and/or a wireless communication module including a transceiver, such as a Bluetooth communication module, to wirelessly communicate with the computing device 12. Therefore, the device may receive and convey data to and from the computing device 12. Other forms of suitable wireless communications technology and protocols can also be employed. The computing device 12 may receive the measurement data, perform analysis on the data, display the data in a desired manner, prepare reports incorporating the data, and log the measurement data, for example.

It is advantageous to combine both spirometry and CO measurement in one handheld device that is portable and can be easily used by the patient at home. The amount of time the patient spends in making measurements is significantly decreased as both parameters are measured simultaneously. The shortened time and wireless communication make the measurement process easy and convenient for the patient. The measurement data can also be easily associated with one particular individual and account and relayed to the health and wellness management system 10. Healthcare professionals may then easily monitor a patient's smoking cessation compliance via a telehealth platform such as system 10 described herein. The handheld device may further incorporate blood pressure and heart rate measurement functions, and additionally an oxygen sensor.

Smoking immediately increases the blood CO level, heart rate (pulse), and blood pressure with decreased and cumulative pulmonary changes. Measuring these parameters in a smoker may motivate them to quit smoking and reinforce cessation benefits as these measurable physiological changes are presented and displayed to the patient. Normal CO level measurements are used to verify smoking cessation compliance which may reduce healthcare insurance premiums. Further, monitoring a population may allow early detection of risky behavior and adaptation for early intervention. An estimated 43.8 million adults smoke cigarettes daily with a total cost in medical and productivity of $193 billion ($96 billion in health expenditures and $97 in productivity loss) or $4,406.39 per smoker. Cigarette smoking is the leading cause of preventable death in the United States and accounts for 440,000 deaths, or one in five. Although the number of adults who smoke has decreased over the last several decades from a peak of 45% of US adults in the mid 1950's, it is still a very costly and risky behavior. Of the over 7,000 chemicals found in tobacco smoke, at least 250 are known to be harmful and at least 69 are known carcinogens. The harmful effects of second hand smoke has also been documented. Therefore, increasing the success of smoking cessation significantly decreases the overall cost of healthcare and improves the health of the general population.

In addition to monitoring and documenting smoking cessation, the computing device 12 may be operable to communicate, preferably wirelessly, with other external monitoring devices adapted to measure physiological parameters indicative of other forms of substance abuse. For example, the external monitoring devices may be used for monitoring blood alcohol content or the presence of illegal drugs and other substances.

Figure 2:
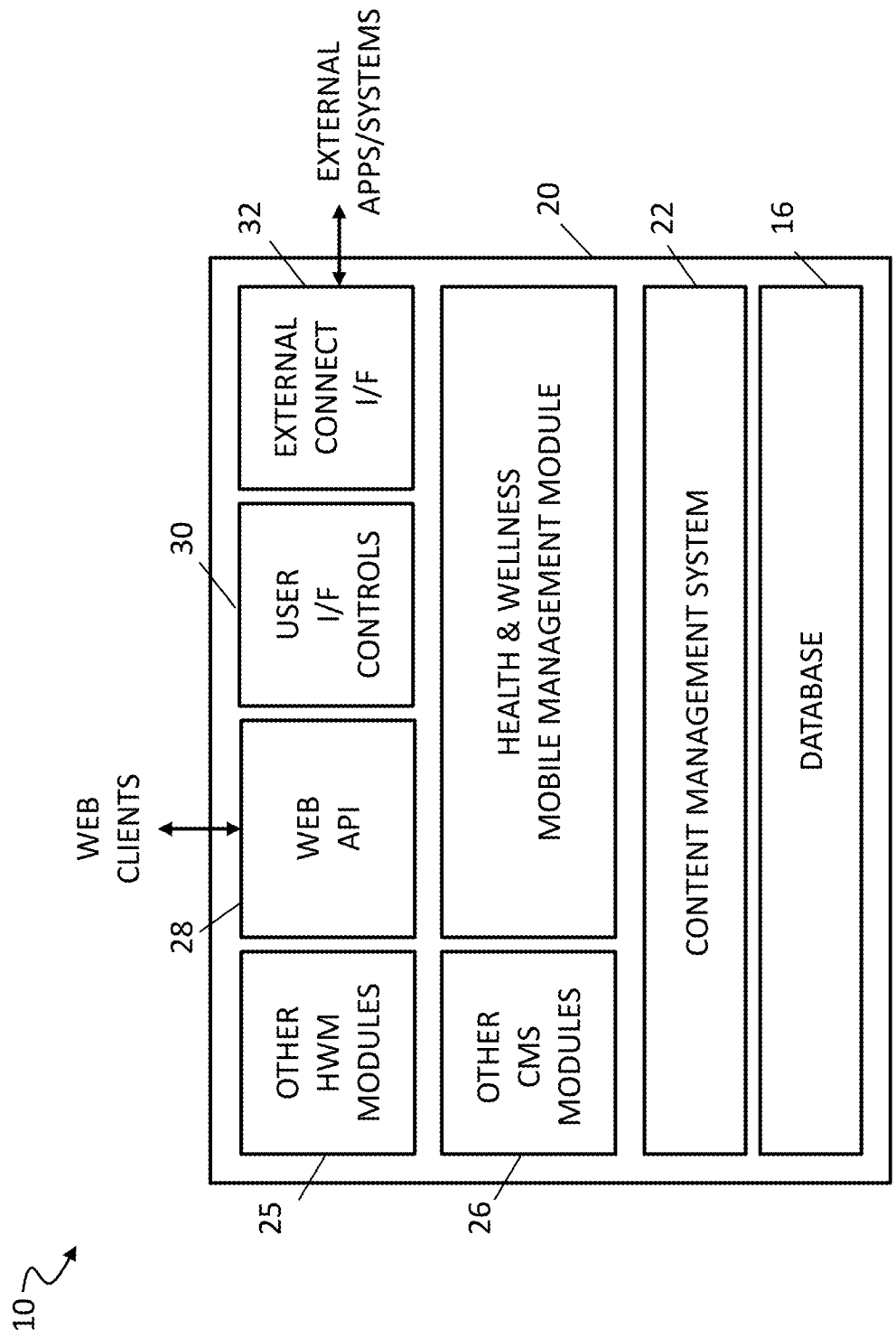
FIG. 2 a simplified block diagram of the health and wellness mobile management system and method according to an exemplary embodiment of the present disclosure.

FIG. 2 a simplified block diagram of the health and wellness mobile management system and method 10 according to an exemplary embodiment of the present disclosure. The exemplary architecture 20 of the health and wellness mobile management system and method 10 comprises a content management system (CMS) 22 that is generally a computer program that allows publishing, editing, and modifying content stored in the database 16. Preferably, all of a patient's data is wholly contained in a single record, where the access to each field of the record can be controlled. The data may be stored in XML or another suitable format. The content management system 22 enables additions of modules or plugins 24 and 26 that extend its functionality, and the content in the database 16 can be edited, published, deleted, and otherwise acted upon by any of the installed modules. One such module is the health and wellness mobile management (WMM) module 24 that provides the primary functions of the system, such as user and role management, medication management, insurance provider policy and information, patient profile data, and supplement information. Other WMM modules 25 may be employed to provide notification and reminder functions for medication pick-up and refills, notifications to healthcare professionals when certain thresholds have been exceeded (e.g., the blood pressure is over a certain limit set by the healthcare professional), for example. The thresholds may be set by a healthcare provider for a particular patient, or set generally for all patients with a certain condition, for example. Using the general population threshold setting, a healthcare provider may screen a population for certain medical conditions such as high blood pressure. The patient/data owner may be encouraged to take certain monitoring measures, such as take his/her own blood pressure once a day, for example. The healthcare provider may choose to not receive any notification, or receive notification only when certain thresholds are exceeded. Additionally, other CMS modules 26 that may be loaded and executed provide additional functionality, such as modules that provide animation on the website, control backend processes like email, user accounts, billing, etc. The health and wellness mobile management module 24, once loaded and executed by the content management system 22, may load additional modules for execution, such as a web API (application programming interface) 28, user interface controls module 30, and external connect interface module 32, for example.

The web API 28 provides a web-based interface to a plurality of web clients such as web browsers and a web mobile management app. The web API 28 may include or provide access to the health and wellness mobile management system website (which may include a separate mobile web site) and services that are operable to interface with web clients for various operating system and platforms, such as Android, Apple iPhone, Windows, etc. The user interface controls module 30 provide additional user interface control and functionality. The external connect interface module 32 provides an interface to external applications and systems that provide, additional health and wellness related functionality, for example, aerobic training, exercise coaching, walking logs, dieting logs, personal healthcare products like blood pressure cuffs, etc.

It should be noted that although the exemplary architecture of the system 10 described above incorporates a CMS, other suitable forms of applications or implementations that permit secured and selected access to published content may be used herein.

Figure 3:
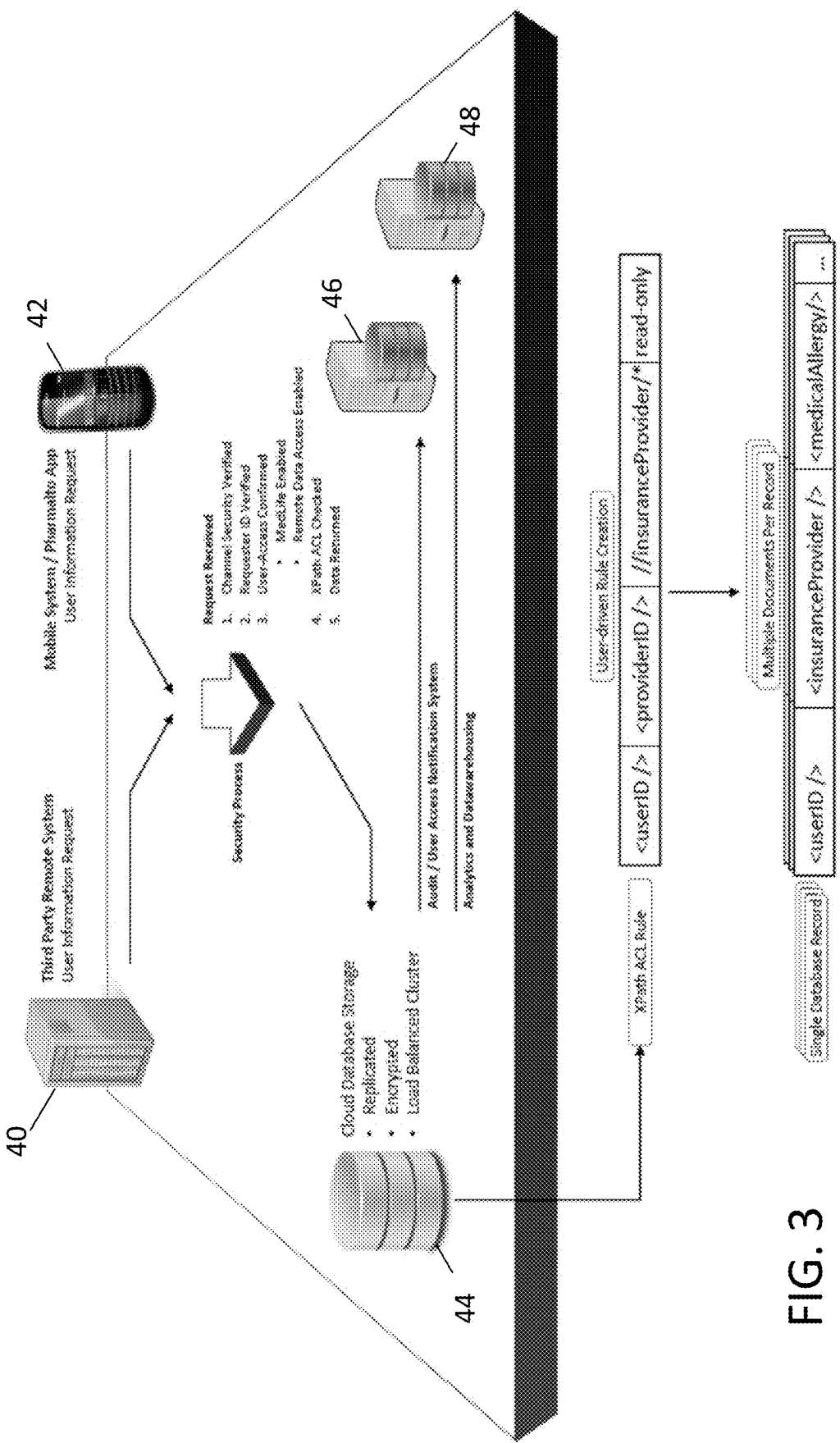
FIG. 3 a simplified data flow diagram illustrating a process of user information request according to an exemplary embodiment of the present disclosure.

FIG. 3 a simplified data flow diagram illustrating a process of user information request according to an exemplary embodiment of the present disclosure. User information requests may come from third party remote systems 40 or mobile computing devices executing the web mobile management app 42, for example. All user information requests must be first screened to ensure proper authentication and verification. This process may include verifying communication channel security, verifying the requester's assigned ID, confirming that the owner of the data has enabled information requests, and verifying against the Access Control List (ACL) that the requester has authorization to access the data. The ACL may define one or more data access levels that define narrow to broad access permission to the data. The patient's data is stored in a cloud database 44, which employs conventional database technologies to provide, for example, redundancy, load balancing, and data encryption. The system 10 also includes an audit database 46 and an analytic database 48. The audit database may store record change logs, system logs, and other audit data that may be necessary to ensure HIPPA compliance, for example. The analytic database 48 warehouses data related to business intelligence and is optimized for data retrieval, aggregation, tabulation, dissemination, and analytics for business intelligence analysis purposes.

A patient's data may be organized as a single record that may consist of multiple documents. Each document and each record is identified with or linked to the patient's or user's identifier, userID. This userID is used to identify the owner of the data, which may be patient or a legal guardian of the patient, for example. In addition, The patient's insurance providers, medicine prescriptions, supplements, and other health and wellness data are stored according to predetermined schema in the multiple documents of the record. These multiple documents comprise the wholly-owned instance of medical record of the patient, and access by any other individual or entity has to be granted permission by the data owner.

Access Control Lists (ACL) or another suitable technique may be used to define and implement rules for users to allow or deny access to any or all parts of the documents in a record. ACL may be used to define roles and the access rights associated with the roles. XPATH expressions may be used to manage the ACL rules as known in the art.

Figure 4:
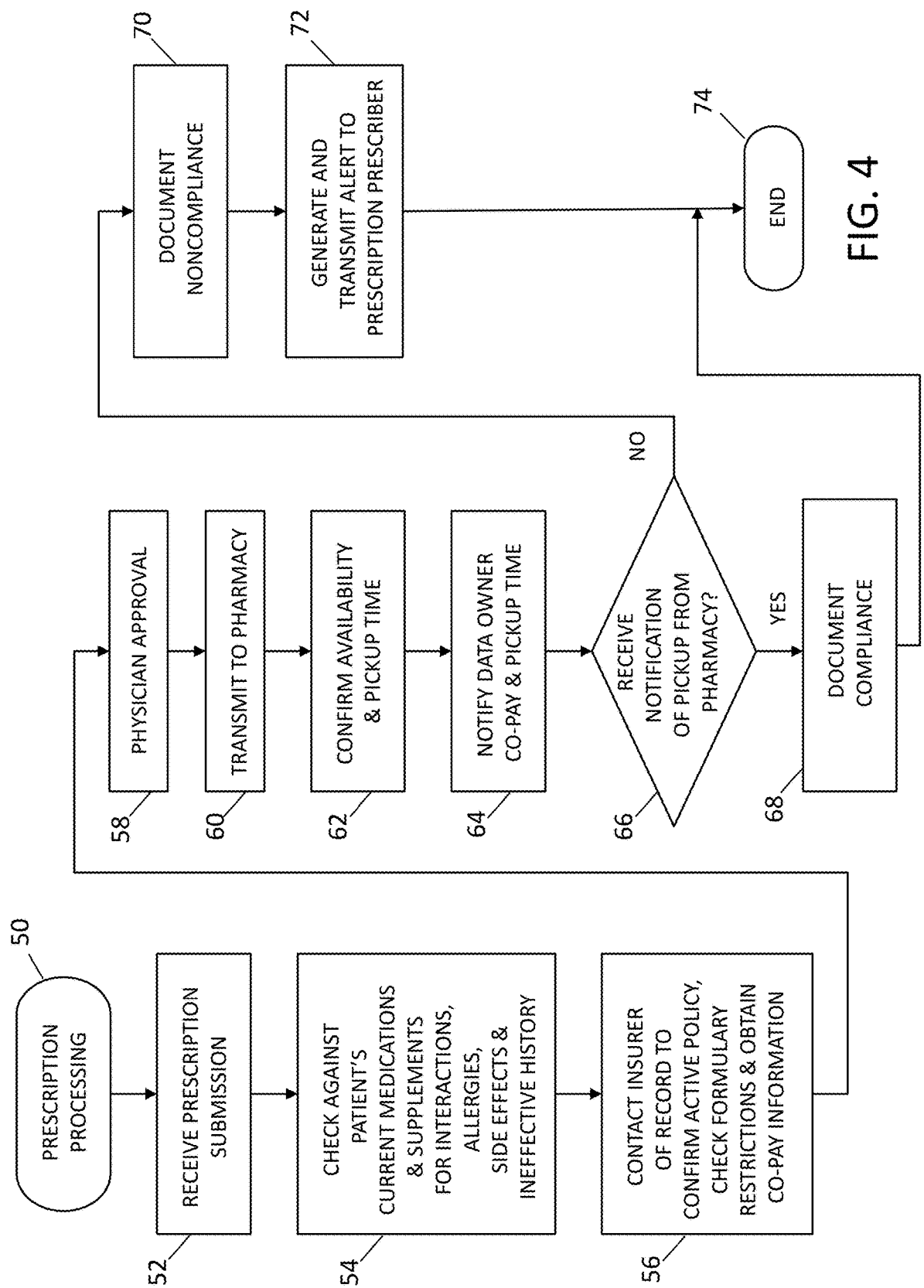
FIG. 4 is a simplified flowchart illustrating a method of electronic prescription processing according to an exemplary embodiment of the present disclosure.

FIG. 4 is a simplified flowchart illustrating a method of electronic prescription processing 50 according to an exemplary embodiment of the present disclosure. The system 10 receives an electronic prescription submitted by the physician, physician assistant, or another personnel at the physician's clinic or office 52. Prior to providing access to the system 10, the person submitting the prescription must log-in to the system via a web-enabled computing device executing a web client such as a browser. After proper log-in, the personnel may enter all data related to the prescribed medication, including but not limited to, the medication name, whether a generic substitute is allowed, dosage, the manner in which the medication should be taken or applied, insurance provider information or selection, pharmacy selection, etc. After the prescription information has been submitted, preliminary verification that all necessary data fields have been filled in properly can also be made prior to proceeding further. It should be noted that some or much of the information does not need to be re-entered each time the prescription is refilled. A patient may have a chronic condition that requires the same medication, and the physician may just need to select the medication from a list of medications associated with the patient. The insurance provider, pharmacy information may also be stored in the system as well and just require confirmation when the physician is submitting the prescription.

In block 54, the received prescription submission is checked against the patient's current medications, supplements, and health history for possible interactions, allergies, side effects, and ineffective history. If any such conditions has been found, it is flagged for review, for example. The physician may select an alternate medication, adjust dosage, etc. in response to the flagged conditions. In block 56, the system 10 contacts the selected insurance provider to confirm that the policy is still active, and further checks for formulary restrictions, and obtain or confirm the co-pay information. Other verifications may also be performed.

Once these verifications have been performed, the physician is requested or alerted for final approval in block 58. This may be done with a push notification on the physician's own computing device that is recognized by the system 10 (by using cookies, IP address, or other mechanisms). Because the prescription submission and prescription approval may be done on different computing devices, an extra layer of security is achieved. After the physician signs off and approves the prescription, the prescription is electronically transmitted to the pharmacy in block 60. Alternatively, an e-prescription service may be used for some of the data verification steps and the interaction with the pharmacy.

In block 62, the system 10 confirms with the pharmacy the availability of the prescribed medication and a pick-up time. In block 64, the owner of the data or the patient is notified of the pick-up time for the medication via his/her computing device by text, email, or another form of communication. The patient may also be notified of the co-pay information. In block 66, the system 10 receives a notification from the pharmacy when the medication has been picked up by the patient. The system 10 may set a time limit as to when the medication should have been picked up, such as three days, for example. The system 10 may also send reminders to the patient if pick up has not occurred within a specific timeframe. Similarly, refill reminders may also be sent. If the medication is picked up within this pre-set time frame, then the system documents compliance in block 68. Otherwise, the non-compliance is documented and a notification is transmitted to the physician that prescribed the medication in blocks 70 and 72. The process ends in block 74. Because prescription non-compliance is a $290 billion problem, the system 10 makes note of any non-compliance and notifies the appropriate individuals or entities when non-compliance is detected.

The system 10 may also employ video capabilities of the computing device to document compliance. The patient may be asked to turn on the video function of the device and record himself/herself when the medication is taken. These videos are recorded and compliance is logged for monitoring. Compliance is especially important for the treatment of certain medical conditions. For example, inconsistent and incomplete treatment is associated with rising drug resistant strains of tuberculosis.

Other types of data may be entered into the system following a similar procedure. The data are entered via a web interface, preferably mobile web interface, and data verification is performed on the fly or after the data are submitted. Suitable notifications or reminders are set according to the type of data entered. Similarly, suitable notifications may be transmitted to individuals or entities depending on the type of data.

Figure 5:
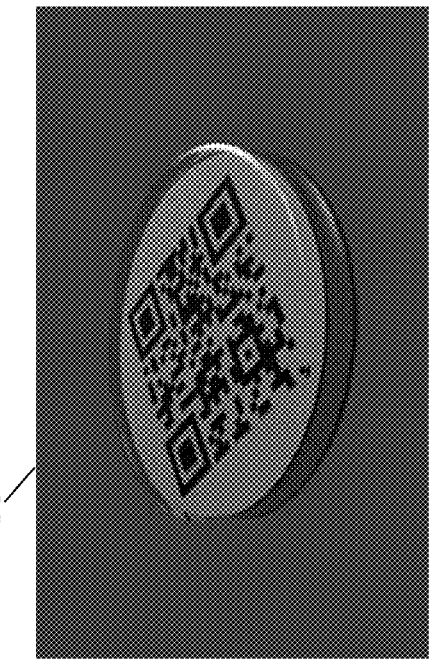
FIG. 5-7 are exemplary views of an ID button that may be incorporated in a variety of accessories to identify a health and wellness mobile management service subscriber according to an exemplary embodiment of the present disclosure.
Figure 6:
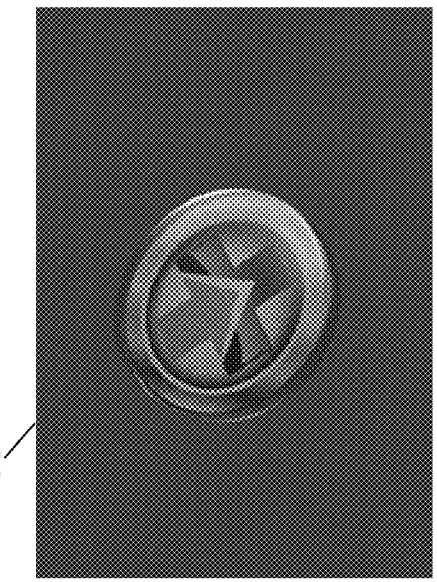
Figure 7:
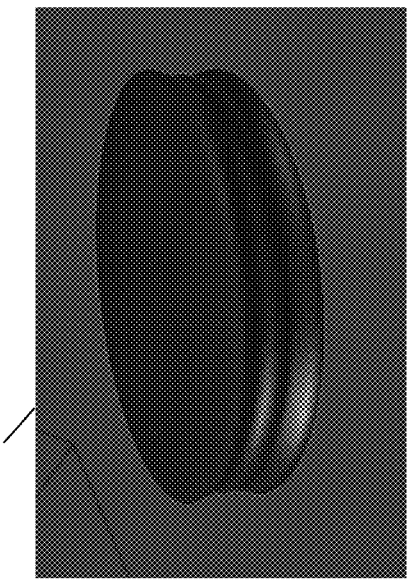

Access to a patient's data may be granted by the patient or data owner. Additionally, access may be granted via automatic recognition of the patient/data owner, such as using biometric data (fingerprints, facial recognition, retina recognition, etc.), near field communication (NFC), or one-dimensional or two-dimensional machine-readable code. FIG. 5-7 are exemplary views of an ID button 80 that may be incorporated in a variety of accessories to identify a health and wellness mobile management service subscriber or user according to an exemplary embodiment of the present disclosure. An exemplary embodiment is an acrylic coated button with a logo identifying the health and wellness mobile management system on one side, and a two-dimensional bar code or QR (Quick Response) code on the second side. Alternatively, RFID (radio frequency identification) technology may be incorporated into the ID button 80. Scanning the code with a code reader application incorporated in a computing device redirects the app to the system website. The patient/data owner may enable this type of data access by emergency personnel, and pre-set the type of information that may be accessible to someone who accesses the system 10 using the ID button. For example, the user may specify that emergency medical information is viewable by a person redirected by the button ID, for example. The emergency medical information may include name, age, gender, an emergency contact name and phone number, medical conditions such as diabetes, heart issues, hypertension, etc., medications, supplements, allergies or sensitivities, past surgeries, etc.

An emergency personnel who has pre-registered to be able to access the health and wellness data in the system 10, and in particular the specific patient/data owner's data can use a pre-assigned code, for example, to gain authorization to access the emergency medical information. When such user attempts to gain access to the data, by using scanning the ID button, for example, the patient/data owner is notified or alerted. Such attempts and subsequent access of the data are logged for audit and reporting purposes. The scanning of the code on the ID button may automatically provide the emergency personnel an emergency contact for the patient/data owner.

Figure 9:
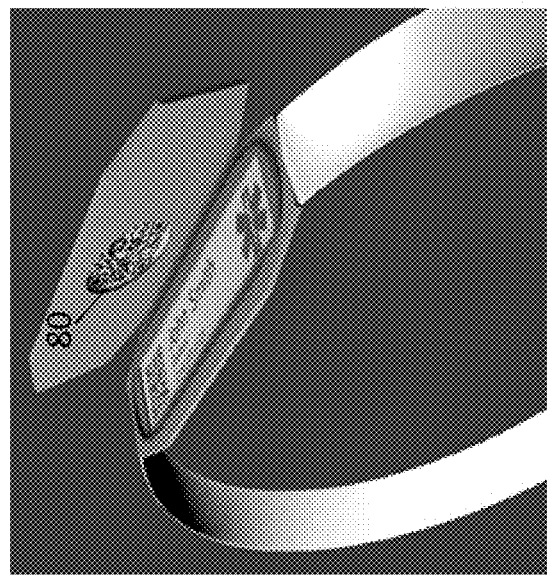
FIGS. 8 and 9 are exemplary views of the ID button incorporated into a bracelet according to an exemplary embodiment of the present disclosure.
Figure 8:

FIGS. 8 and 9 are exemplary views of the ID button 80 incorporated into a bracelet according to an exemplary embodiment of the present disclosure. The button ID may be incorporated into a number of other accessories, such as luggage tag, key chain, medical wrist band, necklace, ring, etc. In the event of an emergency, emergency medical technicians may easily recognize a patient who is a subscriber of the health and wellness mobile management system, and can easily access medical information that may be critical to address the emergency at hand.

The features of the present invention which are believed to be novel are set forth below with particularity in the appended claims. However, modifications, variations, and changes to the exemplary embodiments described above will be apparent to those skilled in the art, and the system and method described herein thus encompass such modifications, variations, and changes and are not limited to the specific embodiments described herein.

What is claimed is:

1. A health and wellness system for a plurality of patients, the system being independent of any healthcare entity and controlling access to health and wellness data soley owned and controlled by each patient, comprising:

a database operable to store a plurality of health and wellness data records associated with a plurality of patients who is respectively the sole owner of the data and has sole control over access authorization and storage of the data, the health and wellness data selected from the group consisting of medicines, supplements, medical history, compliance data, reminders, ineffective medicine, side effects, healthcare provider data, pharmacies, allergies, vaccination record, lifestyle data, exercise data, dietary data, legal documents, medical charts, laboratory data, imaging data, emergency contact data, and insurance data;

a data access control system adapted to strictly control access to the health and wellness data stored in the database according to access rules and authorization soley set by each of the plurality of patients;

a web interface adapted to interface with information requesters submitting requests for entering and accessing data in the health and wellness data records via a web application executable by a computing device selected from the group consisting of mobile telephones, mobile gaming devices, tablet computers, laptop computers, and desktop computers, the information requesters submitting identification information and authorization solely granted by each of the plurality of patients;

the web interface further configured to receive each of the plurality of patients' self-reported data to update the data in the health and wellness data records;

an external connect interface adapted to interface electronically with external systems and applications associated with at least one of physical therapists, emergency medical technicians, healthcare providers, pharmacies, hospitals, emergency rooms, acute care facilities, laboratories, outpatient surgery centers, benefits manager and insurer content management systems, and third party live data analysis systems for receiving health and wellness data associated with the patient for storing in the health and wellness data in the database;

the external connect interface further configured to interface electronically with a personal health monitoring device for receiving additional health and wellness data associated with each patient for storing in the health and wellness data in the database;

a prescription interface in communication with the database adapted to receive a pharmaceutical prescription for a prescribed medication for the patient submitted by a healthcare provider, verify the submitted pharmaceutical prescription against data in the patient's health and wellness data records, request and receive approval for the submitted pharmaceutical prescription, and monitor patient compliance including receiving the prescribed medication and following instructions in using the prescribed medication;

a patient identification device in the form of a wearable accessory adapted to automatically and uniquely identify each of the plurality of patients as the data owner of the health and wellness data records stored in the database, and to grant access to the data in response to detecting the patient identification device and verifying patient identification data automatically transmitted by the patient identification device, the patient identification device operable to automatically direct the web application to access at least a data subset of the health and wellness data stored in the database upon recognition of access being granted; and a physiological parameter measurement device adapted to wirelessly communicate with the external connect interface, the physiological parameter device operable to measure a physiological parameter of the patient, and transmit the measurement data via the external connect interface for storing in the health and wellness data in the database.

2. The system of claim 1, wherein the health and wellness data record comprise data in Extensible Markup Language (XML) format.

3. The system of claim 1, wherein the access rules are specified by an access control list.

4. The system of claim 1, wherein the patient identification device comprises an accessory bearing machine-readable code identifying the patient.

5. The system of claim 1, wherein the patient identification device comprises an accessory bearing a two-dimensional machine-readable code identifying the patient.

6. The system of claim 1, wherein the patient identification device comprises an accessory bearing Radio Frequency Identification (RFID) identifying the patient.

7. The system of claim 1, wherein the patient identification device comprises a biometric characteristic reader.

8. The system of claim 1, wherein the patient identification device comprises a Near Field Communication (NFC) device.

9. The system of claim 1, wherein the web interface is adapted to automatically notify a healthcare professional at the request and authorization of the patient when certain patient health data exceed thresholds.

10. The system of claim 9, wherein the web interface is adapted to receive a setting of health data thresholds from the healthcare professional at the request and authorization of the patient.

11. The system of claim 1, wherein the web interface is adapted to automatically transmit a notification to a healthcare professional when a certain monitored patient condition requires attention at the request and authorization of the patient.

12. The system of claim 1, wherein the physiological parameter measurement device is configured to measure a volume of air inhaled and exhaled by the patient and a carbon monoxide content in the exhaled air as an assessment of smoking cessation compliance.

13. A method for health and wellness comprising:
providing strictly-controlled access to a database operable to store health and wellness data associated with a plurality of patients who are the sole owners of his/her respective health and wellness data in the database and each patient has sole control over access authorization and storage of his/her own health and wellness data, the health and wellness data selected from the group consisting of medicines, supplements, medical history, compliance data, reminders, ineffective medicine, side effects, healthcare provider data, pharmacies, allergies, vaccination record, lifestyle data, exercise data, dietary data, legal documents, medical charts, laboratory data, imaging data, emergency contact data, and insurance data, the access to the health and wellness data according to access rules set by each patient;

interfacing with information requesters including the plurality of patients submitting requests for entering, updating, and accessing the health and wellness data via a web application executable on a mobile device, the information requesters submitting identification information and authorization granted by each patient;

interfacing electronically with external systems and applications associated with at least one of physical therapists, emergency medical technicians, healthcare providers, pharmacies, hospitals, emergency rooms, acute care facilities, laboratories, outpatient surgery centers, benefits manager and insurer content management systems, and third party live data analysis systems for receiving health and wellness data associated with the plurality of patients for storing in the health and wellness data in the database;

further interfacing electronically with a personal health monitoring device for receiving additional health and wellness data associated with the plurality of patients for storing in the health and wellness data in the database;

receiving, by a prescription interface, a pharmaceutical prescription for a prescribed medication for the plurality of patients submitted by a healthcare provider, verifying the submitted pharmaceutical prescription against data in the patient's health and wellness data, requesting and receiving approval for the submitted pharmaceutical prescription, and monitoring patient compliance including receiving the prescribed medication and following instructions in using the prescribed medication;

detecting and receiving identification data from a patient identification device in the form of a wearable accessory adapted to uniquely identify the patient as the data owner of the health and wellness data record stored in the database and to grant access to the data in response to detecting the patient identification device, the patient identification device operable to automatically direct the web application to access at least a data subset of the health and wellness data stored in the database upon recognition of access being granted; and receiving, from a mobile physiological parameter measurement device, physiological data of a plurality of patients, and storing the measurement data in the health and wellness data in the database.

14. The method of claim 13, comprising:
receiving an information request from an information requester;
verifying channel security of the information request;
verifying requester identifier;
confirming authorization for information requester to access the health and wellness data record;
confirming remote access to the health and wellness data record is authorized;
verifying the access rules; and
transmitting requested data to the information requester.

15. The method of claim 13, comprising receiving an information request from an information requester, wherein the information request comprises a machine-readable code identifying the patient and data owner of the health and wellness data record.

16. The method of claim 13, comprising receiving an information request from an information requester, wherein the information request comprises a two-dimensional machine-readable code identifying the patient and data owner of the health and wellness data record.

17. The method of claim 13, comprising specifying the access rules by an access control list.

18. The method of claim 13, comprising receiving an information request from an information requester via the web application executing on a computing device selected from the group consisting of mobile telephones, gaming devices, tablet computers, laptop computers, and desktop computers.

19. The method of claim 13, further comprising transmitting a notification to the healthcare provider in response to patient non-compliance.

20. The method of claim 13, further comprising transmitting a notification to the healthcare provider in response to a patient health data exceeding a threshold set by the healthcare provider.

21. The method of claim 13, further comprising checking the pharmaceutical prescription against the patient's health and wellness data for adverse conditions that may result.

22. The method of claim 13, further comprising videoing the patient to document and monitor compliance.

23. The method of claim 13, further comprising automatically transferring ownership of the health and wellness data associated with a minor upon reaching adulthood.

24. The method of claim 13, further comprising:
setting a general population threshold for a certain health parameter; and
monitoring for patient self-monitoring activities to screen for the certain data parameter exceeding the general population threshold.

25. The method of claim 13, wherein receiving measurement data comprises receiving measurement data associated with a volume of air inhaled and exhaled by the patient and a carbon monoxide content in the exhaled air as an assessment of smoking cessation compliance.

26. A non-transitory computer-readable medium having encoded thereon a method for health and wellness, the method comprising:
providing strictly-controlled access to a database operable to store a plurality of health and wellness data records associated with a plurality of patients who are the sole owners of his/her respective health and wellness data in the database and has sole control over access authorization and storage of his/her own health and wellness data, the health and wellness data selected from the group consisting of medicines, supplements, medical history, compliance data, reminders, ineffective medicine, side effects, healthcare provider data, pharmacies, allergies, vaccination record, lifestyle data, exercise data, dietary data, legal documents, medical charts, laboratory data, imaging data, emergency contact data, and insurance data, the access to the health and wellness data records according to access rules set by each patient;
interfacing with information requesters submitting requests for entering and accessing the health and wellness data via a web application, the information requesters submitting identification information and authorization granted by each patient;
interfacing with external systems and applications associated with at least one of physical therapists, emergency medical technicians, healthcare providers, pharmacies, hospitals, emergency rooms, acute care facilities, laboratories, outpatient surgery centers, benefits manager and insurer content management systems, and third party live data analysis systems for receiving health and wellness data associated with the plurality of patients for storing in the health and wellness data in the database;
further interfacing electronically with a personal health monitoring device for receiving additional health and wellness data associated with the plurality of patients for storing in the health and wellness data in the database;
receiving, by a prescription interface, a pharmaceutical prescription for a prescribed treatment for at least one of the plurality of patients submitted by a healthcare provider, verifying the submitted pharmaceutical prescription against data in the patient's health and wellness data, requesting and receiving approval for the submitted pharmaceutical prescription, and monitoring patient compliance including receiving the prescribed treatment and following instructions for the prescribed treatment;
detecting and receiving identification data from a patient identification device in the form of a wearable accessory adapted to uniquely identify each patient as the data owner of the health and wellness data stored in the database and to grant access to the data in response to detecting the patient identification device, the patient identification device operable to automatically direct the web application to access at least a data subset of the health and wellness data stored in the database upon recognition of access being granted; and
receiving, from a physiological parameter measurement device, measurement data associated with a volume of air inhaled and exhaled by at least one of a plurality of patients and a carbon monoxide content in the exhaled air as an assessment of smoking cessation compliance, and storing in the health and wellness data in the database.

* * * * *